United States Patent [19]

Mattheck et al.

[11] Patent Number: 4,784,127
[45] Date of Patent: Nov. 15, 1988

[54] DEVICE FOR FIXING THE FRACTURED ENDS OF A BONE

[75] Inventors: Claus Mattheck, Leimersheim; Martin Börner, Schwalbach, both of Fed. Rep. of Germany

[73] Assignee: Kernforschungszentrum Karlsruhe GmbH, Karlsruhe, Fed. Rep. of Germany

[21] Appl. No.: 837,275

[22] Filed: Mar. 7, 1986

[30] Foreign Application Priority Data

Jan. 18, 1986 [DE] Fed. Rep. of Germany ....... 3601344

[51] Int. Cl.⁴ .............................................. A61F 5/04
[52] U.S. Cl. ............................................. 128/92 YP
[58] Field of Search .......... 128/92 Y, 92 YY, 92 YX, 128/92 YP, 92 YPM, 92 YF

[56] References Cited

U.S. PATENT DOCUMENTS 4,297,993 11/1981 Harle .............................. 128/92 YP

FOREIGN PATENT DOCUMENTS 0118778 9/1984 European Pat. Off. ....... 128/92 YY
2609723 7/1977 Fed. Rep. of Germany ........ 128/92 YY
0611147 5/1979 Switzerland ................... 128/92 YP Primary Examiner—Richard J. Apley
Assistant Examiner—David J. Isabella
Attorney, Agent, or Firm—Spencer & Frank

[57] ABSTRACT

Device for holding together the fractured ends of a bone in a living body, including an elongate holding member arranged to be secured to the bone and provided, for this purpose, with openings for holding connecting elements, with a certain elasticity being retained, and reinforcement members forming a unit with the holding member, extending in the length direction of the holding member and disposed along opposite sides of each opening.

3 Claims, 2 Drawing Sheets

DEVICE FOR FIXING THE FRACTURED ENDS OF A BONE

BACKGROUND OF THE INVENTION

The present invention relates to a device for fixing the fractured ends of a bone in a living body by means of a nail or a plate which is connected with the bone.

Marrow nailing and the external application of long plates are generally known and medically tested procedures for fixing fractures in long bones. The nails, generally, either have a continuous slot and a cloverleaf-type cross section, or have a circular cross section and a slot which ends in the upper region of the nail.

The significant drawback of a nail having a continuous slot is that, on the one hand, for biomechanical reasons and due to the provision of the slot and the requirements for elasticity, the nail has a cloverleaf configuration but, on the other hand, comes into contact with the bone wall only in very limited longitudinal regions, i.e. is lacking as regards transverse clamping in the femur.

A comparatively high rate of cracks and tearing has been found with nails having a noncontinuous slot and a partially circular cross section.

The cracks always start at the end of the slot, and in the plate they start between two bores for the connecting elements. In the interlocking nail, they start at the holes for the transverse bolts. As a result of experimental tests and study, it has been found that a finite slot, in particular, in which the flow of forces is deflected around the end of the slot, enhances crack formation.

Providing the slot end with an additional notch, as had been done in the past to prevent crack formation, makes this effect even worse.

SUMMARY OF THE INVENTION

It is an object of the present invention to provide a nail or plate of the above-mentioned type which is configured to have a biomechanically favorable shape and to prevent crack and tear formation.

The above and other objects are achieved, according to the present invention, by an improved device for holding together the fractured ends of a bone in a living body, the device includes an elongate holding member arranged to be secured to the bone and provided, for this purpose, with openings for holding connecting elements, with a certain elasticity being retained, and reinforcement members forming a unit with the holding member, extending in the length direction of the holding member and disposed along opposite sides of each opening.

DESCRIPTION OF THE PREFERRED EMBODIMENTS

Figure 1:
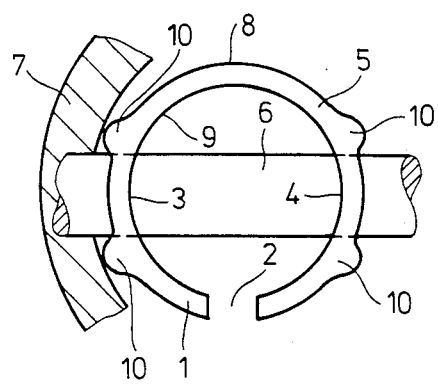
FIGS. 1 and 2 are axial end views of two embodiments of nails according to the invention.
Figure 2:
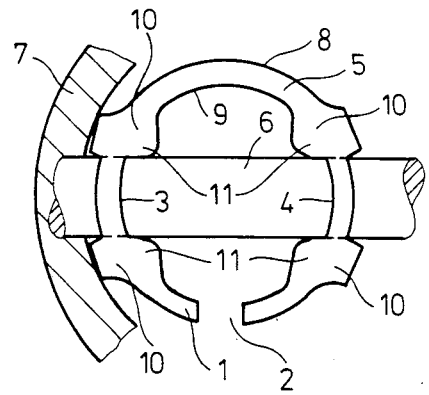

FIGS. 1 and 2 are end views of two embodiments of hollow nails 1 according to the invention. Each nail 1 has a continuous slot 2 which extends over its full length, i.e. from its head to its tip. In cross section, the inner and outer peripheries of each embodiment are basically circular. Each nail is composed of a nail wall 5 which is provided with pairs of openings 3 and 4 spaced a defined distance axially along nail 1. Each pair of openings is provided to receive a transverse bolt, interlocking element or screw 6 to fix nail 1 in the interior of a bone 7 (not shown in detail) in an elastic manner with respect to the bone. The axial spacing between pairs of openings 3, 4 is selected according to principles known in the art.

From extensive examinations and studies it has now been found that crack formation in the region of the openings 3 and 4 can be prevented by providing reinforcements 10 and/or 11, at least in the region of the openings 3 and 4, on the outer wall face 8 and/or the inner wall face 9, on both sides of openings 3 and 4, extending in the axial direction of nail 1. These reinforcements have a bead shape. Length, thickness, width and other dimensions of reinforcements 10, 11 depend on the material of nail 1 and the requirements to be met.

The embodiment shown in FIG. 2 differs from that of FIG. 1 with regard to the shape of external reinforcements 10 and the provision of internal reinforcements 11.

Figure 3:
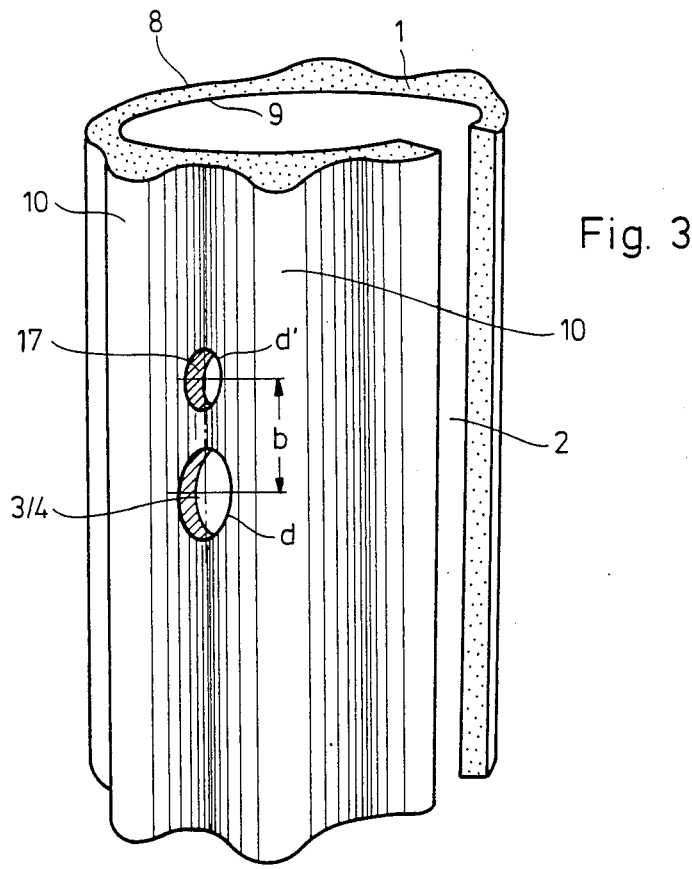
FIG. 3 is a perspective view of the embodiment of FIG. 1.

The physical relationship between reinforcements 10 and opening 3, for example, is shown again more clearly in FIG. 3. For manufacturing reasons, it is of advantage to make reinforcements 10 and 11 continuous to extend along the entire length of the nail. For nails 1 having external diameters between 9 and 16 mm, a length of 300 to 500 mm and a wall thickness of about 1 mm, the radial thickness of reinforcements 10 and 11 is preferably 1.05 to 3 times this wall thickness.

Openings 3 and 4 required by this structure produce stress concentrations which could reduce load carrying capability. For that reason, a further feature of the present invention involves the provision, in the vicinity of each opening 3, 4, of at least one further relief bore 17 which is spaced along the nail axis from a respective opening 3 or 4 and may be above or below the associated opening. The shape, size and position of relief bore 17 are optimized in such a manner that the stress peaks occurring at each bore 17 equals, as closely as possible, the reduced stress at the associated opening 3, 4. Optimally, the diameter $d'$ of each relief bore 17, should range between $\frac{1}{4} d \leq d' \leq d$, where d is the diameter of the associated opening 3 or 4. The distance b from the center of an opening 3 or 4 and to the center of its associated relief bore 17 is preferably in the range of $d \leq b \leq 3d$.

Reinforcements 10 and 11 are shaped and dimensioned to take into account that nail 1 must have sufficient elasticity to enable it to be safely hammered into the interior of a bone over a slightly curved path without risk of breakage to the bone.

Figure 4:
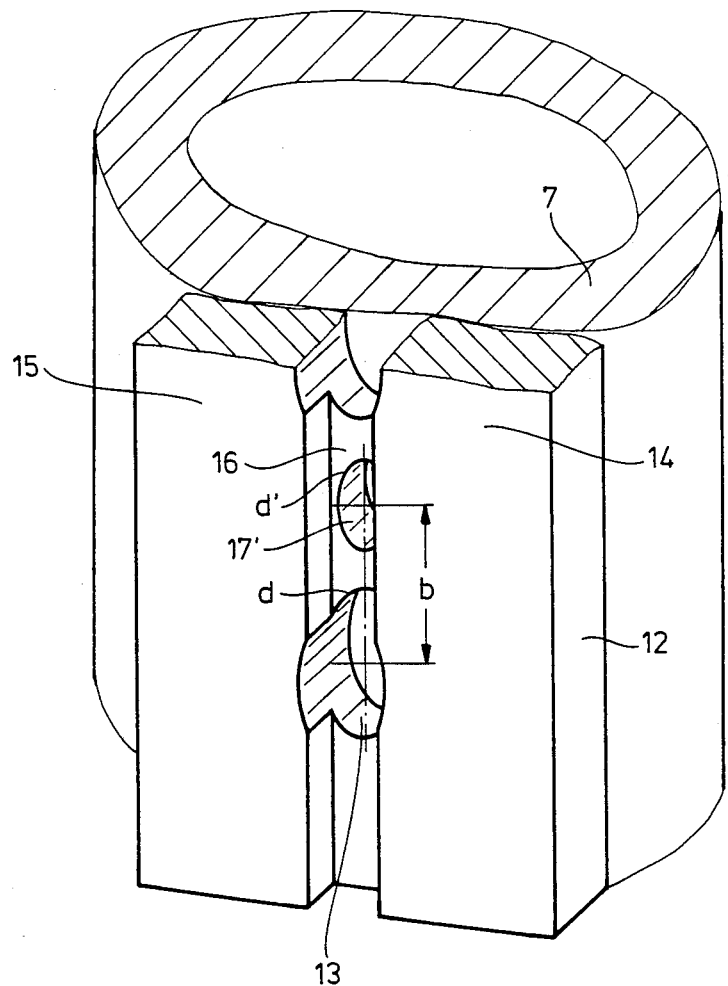
FIG. 4 is a perspective detail view of a portion of an embodiment of a plate according to the invention.

FIG. 4 shows part of an embodiment of a plate 12 according to the invention which is fixed externally to a bone 7 by means of screws passing through holes, or openings, 13 that are analogous to openings 3 and 4 of FIGS. 1–3. To prevent crack formation in such a hole, plate 12 is provided with mutually parallel, axially extending reinforcements 14 and 15 which extend, precisely like reinforcements 10, 11 in the example of nail 1 according to FIGS. 1 to 3, at least in the region of hole 13, along both sides of the or each hole 13. These reinforcements 14, 15 may also be produced by cutting a groove 16 along an initially thick plate 12 so that groove 16 extends a sufficient distance beyond holes 13. Although this groove 16 reduces the thickness of the plate, it surprisingly does not weaken, but instead reinforces, plate 12 in the sense of preventing cracks. A typical embodiment of plate 12 has a thickness, i.e. in the region of groove 16, between 2 and 7 mm, and a width between 5 and 25 mm. The thickness of reinforcements 14 and 15 corresponds to the radial thickness of reinforcements 10 and 11. A relief bore 17' is disposed above or below hole 13 and the preferred values for b, d and d' are as described above with reference to FIG. 3. Preferably, a further relief bore 17 (not shown) should be provided, for reasons of symmetry of the flow of forces, at the other side of hole 13.

Reinforcements 14 and 15 are shaped and dimensioned to assure that plate 12 has sufficient elasticity to not interfere with the bore healing process. Some pressure, or load, must exist between the fractured bone ends in order for healing to proceed normally. If the fracture region were supported completely rigidly, healing will be delayed.

Thus, the indication herein that the nail or plate is contracted so that a certain elasticity is retained means that the device must be hard enough to maintain the fractured bone parts in position relative to one another, while the plate must be soft enough to enable the fractured ends to press together and the nail must be soft enough to be hammered in and follow a slightly curved path. The required elasticity and the manner of achieving it are well known in the art.

The overall length of nail 1 or plate 12 is selected according to principles known in the art on the basis of the specific application.

As in the embodiment of FIGS. 1-3, the size, shape and position of bores 17' are optimized in such a manner that the stress peaks occurring at bores 17' equal, as closely as possible, the reduced stress at openings 13.

As shown in FIGS. 1-3, the reinforcements may be located directly adjacent the boundaries of openings 3, 4, or, as shown in FIG. 4, may slightly overlap those boundaries.

Each opening 3, 4 and 13 may typically have a diameter of 5 mm. Nail 1 and plate 12 may be made of a suitable biocompatible material such as a biocompatible stainless steel or a biocompatible fiber reinforced composite.

It will be understood that the above description of the present invention is susceptible to various modifications, changes and adaptations, and the same are intended to be comprehended within the meaning and range of equivalents of the appended claims.

What is claimed is:

1. A device for holding together fractured ends of a bone in a living body, said device comprising: a nail in the form of a hollow tube arranged to be secured to the bone, having a length dimension which will extend parallel to the axis of the bone when said nail is secured to the bone; said nail including inner and outer wall surfaces and a substantially uniform wall thickness throughout, a continuous slot extending axially along the entire length dimension of the nail, at least one pair of substantially diametrically opposed openings for holding connecting elements, with a certain elasticity being retained; and reinforcement members in the form of beads forming a unit with said nail, extending in the direction of said length dimension of said nail and disposed adjacent said openings.

2. Device as defined in claim 1 wherein said nail is further provided with at least one relief bore associated with one said opening and spaced from the associated opening in the direction of the length dimension of said holding nail.

3. Device as defined in claim 2 wherein said relief bore has a diameter d', said opening associated with said relief bore is a bore having a diameter d, said relief bore and said one opening have centers which are spaced apart by a distance b, and d, d' and b are related by:

$$\tfrac{1}{4}d \leq d' \leq d, \text{ and}$$

$$d \leq b \leq 3d.$$

* * * * *